United States Patent
Kline et al.

[11] Patent Number: 5,735,840
[45] Date of Patent: Apr. 7, 1998

[54] DISPOSABLE DIAPER WITH INTEGRAL BACKSHEET LANDING ZONE

[75] Inventors: Mark J. Kline; David J. K. Goulait, both of Cincinnati, Ohio

[73] Assignee: The Procter & Gamble Company, Cincinnati, Ohio

[21] Appl. No.: 748,853

[22] Filed: Nov. 14, 1996

Related U.S. Application Data

[63] Continuation-in-part of Ser. No. 717,473, Sep. 20, 1996.

[51] Int. Cl.⁶ .................................................. A61F 13/15
[52] U.S. Cl. ..................... 604/391; 604/385.1; 604/386
[58] Field of Search ........................... 604/385.1, 386, 604/387, 389–391

[56] References Cited

U.S. PATENT DOCUMENTS

| | | | |
|---|---|---|---|
| 3,955,575 | 5/1976 | Okuda | 604/391 |
| 4,410,327 | 10/1983 | Baggaley | 604/391 |
| 4,568,342 | 2/1986 | Davis | 604/391 |
| 4,725,473 | 2/1988 | Van Gompel et al. | |
| 5,032,122 | 7/1991 | Noel et al. | 604/391 |
| 5,151,092 | 9/1992 | Buell et al. | 604/385.2 |
| 5,256,231 | 10/1993 | Gorman et al. | |
| 5,318,555 | 6/1994 | Siebers et al. | 604/390 |
| 5,326,612 | 7/1994 | Goulait . | |
| 5,380,313 | 1/1995 | Goulait et al. | 604/390 |
| 5,407,439 | 4/1995 | Goulait | 604/391 |
| 5,470,417 | 11/1995 | Goulait . | |
| 5,547,531 | 8/1996 | Allen et al. . | |
| 5,615,460 | 4/1997 | Weirich et al. | 604/391 |

FOREIGN PATENT DOCUMENTS

| | | |
|---|---|---|
| 0 604 731 A1 | 7/1994 | European Pat. Off. . |
| WO 92/01401 | 2/1992 | WIPO . |
| WO 94/08789 | 4/1994 | WIPO . |

*Primary Examiner*—Mark O. Polutta
*Attorney, Agent, or Firm*—David M. Weirich; Steven W. Miller; Jacobus C. Rasser

[57] ABSTRACT

A disposable absorbent article having an integral landing zone. The absorbent article includes a liquid pervious topsheet, a liquid impervious backsheet joined with the topsheet and an absorbent core located between the topsheet and the backsheet. The backsheet includes a laminate of an inner web and an outer web, wherein at least a portion of the inner web is juxtaposed the garment surface of the absorbent core. The outer web includes an integral landing zone having portions mechanically prestrained to provide raised elements capable of entangling the engaging components of a complementary male fastening component. The inner web and the outer web are continuously laminated with each other except where the raised elements provide the integral landing zone.

30 Claims, 4 Drawing Sheets

DISPOSABLE DIAPER WITH INTEGRAL BACKSHEET LANDING ZONE

This application is a continuation-in-part of application Ser. No. 08/717,473, filed on Sep. 20, 1996, which is pending.

FIELD OF THE INVENTION

The present invention relates to a backsheet for disposable absorbent articles, and more particularly, to a backsheet including an integral landing zone.

BACKGROUND OF THE INVENTION

Refastenable fastening devices of the hook and loop type are currently used widely in clothing, disposable absorbent articles, and the like. Such devices are used when it is desirable to create a refastenable bond between two or more articles or between several surfaces of the same article. In certain applications, these refastenable fastening devices have replaced conventional buckles, zippers, buttons, snaps, tie fasteners or sewing.

One popular type of mechanical fastener currently in wide use which utilizes mechanical entanglement to create a refastenable bond is sold under the trademark VELCRO. VELCRO fastening devices are described in greater detail in U.S. Pat. No. 2,717,437; U.S. Pat. No. 3,009,235; U.S. Pat. No. 3,266,113; U.S. Pat. No. 3,550,837; U.S. Pat. No. 4,169,303; and U.S. Pat. No. 4,984,339.

VELCRO type fasteners generally utilize two components. A male component and a female component. The male and female components are often referred to as the hook and loop components, respectively. The male component generally contains a plurality of resilient, upstanding loop shaped elements. The female component generally consists of a fabric containing a plurality of upstanding loops. When the male component and female component are pressed together in a face to face relationship to close the fastening device, the hooks entangle the loops forming a plurality of mechanical bonds between the hook and loop components.

Hook and loop type mechanical fastening devices have been found especially useful on disposable absorbent articles such as disposable diapers, adult incontinence garments, feminine hygiene garments, training pants and the like. However, the use of existing refastenable hook and loop type fastening devices on such disposable absorbent articles has been limited due to the cost of the fasteners relative to other fastener types. Although several attempts have been made to reduce the cost of hook and loop type fasteners suitable for use on disposable absorbent articles, the attempts have generally suffered from the drawback that the hooks and loops must be manufactured separately from the disposable absorbent article and joined thereto during manufacturing. Therefore, in order to reduce cost and to increase manufacturing speeds, it would be advantageous to provide a landing zone which is integral with one component of the disposable absorbent article.

Thus, it is an object of the present invention to provide an improved fastening device for disposable absorbent articles.

It is another object of the present invention to provide a backsheet for a disposable absorbent article including an integral landing zone.

It is yet another object of-the present invention to provide a method of making a backsheet for a disposable absorbent article including an integral landing zone for a hook and loop type fastening device.

These and other objects of the present invention will be more readily apparent when considered with reference to the following description and when taken in connection with the accompanying drawings.

SUMMARY OF THE INVENTION

The present invention relates to disposable absorbent articles having integral landing zones. In preferred embodiments, the absorbent article includes a liquid pervious topsheet, a liquid impervious backsheet joined with the topsheet and an absorbent core located between the topsheet and the backsheet. The backsheet preferably includes a laminate of an inner web and an outer web, wherein at least a portion of the inner web is juxtaposed the garment surface of the absorbent core. The outer web includes an integral landing zone having portions mechanically prestrained to provide raised elements capable of entangling the engaging components of a complementary male fastening component. The inner web and the outer web are preferably continuously joined with each other except where the raised elements provide the integral landing zone.

DETAILED DESCRIPTION OF THE INVENTION

Figure 1:
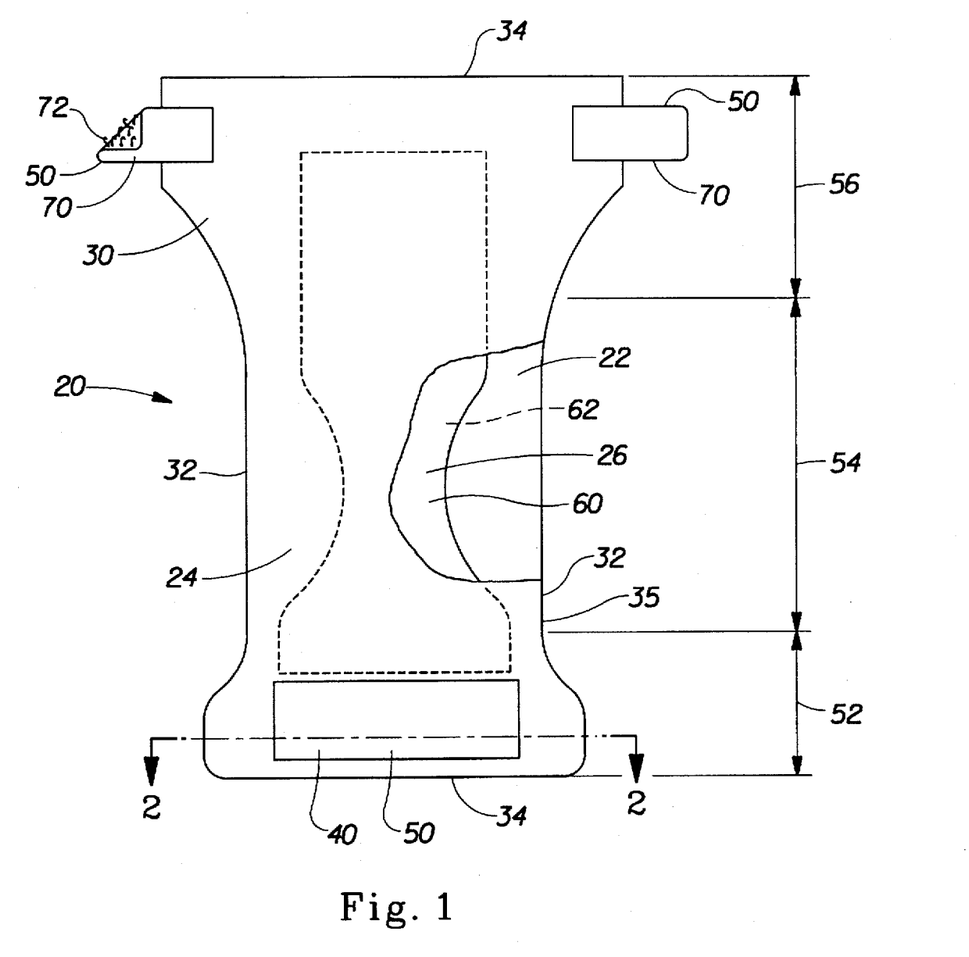
FIG. 1 is a perspective view of a disposable diaper that includes one embodiment of the backsheet of the present invention including the integral landing zone.

As used herein the term "absorbent article" refers to articles which absorb and contain body exudates and more specifically refers to articles which are placed against or in proximity to the body of the wearer to absorb and contain various exudates discharged from the body. Absorbent articles are typically differentiated by whether they are reusable or disposable. "Disposable" refers to articles which are generally intended to be discarded after a single use (i.e., they are not generally intended to be laundered or otherwise restored or reused). The absorbent articles of the present invention are preferably disposable absorbent articles. The absorbent articles may be further defined by whether they are "unitary" such that they do not require a separate manipulative parts or whether they comprise an element of a diaper system such as a separate holder and liner. The absorbent articles of the present invention are preferably unitary. One preferred embodiment of a unitary disposable absorbent article of the present invention, diaper 20, is shown in FIG. 1. As used herein, the term "diaper" refers to a garment generally worn by infants and/or incontinent persons about the lower torso to receive and contain bodily exudates. It should be understood, however, that the present invention is also applicable to other disposable absorbent articles such as incontinence briefs, undergarment absorbent inserts, disposable training pants, belted diapers, diaper holders, sanitary napkins, and the like.

FIG. 1 is a plan view of one embodiment of a diaper 20 in its flat out, uncontracted state (i.e., without elastic induced contraction pulled out) with portions of the structure being cut away to more clearly show the underlying structure of the diaper 20 and with the portion of the diaper 20 which contacts the wearer facing away from the viewer. The diaper 20 is shown in FIG. 1 to have a front waist region 52, a rear waist region 56, and a crotch region 54 located between the from waist region 52 and the rear waist region 56. The waist regions generally comprise those portions of the diaper 20 which, when worn, encircle the waist of the wearer. The waist regions may include an elastic element such that they gather about the waist of the wearer to provide improved fit and containment. The crotch region 54 is that portion of the diaper 20 positioned between the front waist region 52 and the rear waist region 56 which, when the diaper is worn, is generally positioned between the legs of the wearer.

The diaper 20 preferably comprises a liquid pervious topsheet 22, a liquid impervious backsheet 24 and an absorbent core 26 which is preferably located between the topsheet 22 and the backsheet 24. The absorbent core 26 preferably has a garment surface 60 which generally faces away from the wearer and a body surface 62 which generally faces the wearer. The diaper 20 preferably also includes a hook and loop type fastening system 50 including at least one engaging component 70 (male fastening component) and at least one landing zone 40 (female fastening component). The diaper 20 may also include such other features as are known in the art including leg cuffs, front and rear ear panels, waistcap features, elastics and the like to provide better fit, containment and aesthetic characteristics. Such additional features are well known in the art and are described in U.S. Pat. No. 3,860,003; and U.S. Pat. No. 5,151,092 which are incorporated by reference herein.

In a preferred embodiment of the diaper 20 in which the backsheet 24 has length and width dimensions generally larger than those of the absorbent core 26, the backsheet 24 extends beyond the edges of the absorbent core 26 to thereby form the periphery 35 of the absorbent article. The periphery 35 defines the outer perimeter, in other words, the edges of the diaper 20. The periphery 35 comprises the longitudinal edges 32 and the end edges 34. As shown in FIG. 1, the topsheet 22 may be coterminous with the backsheet 24 along the end edges 34 as well as the longitudinal edges 32 of the diaper 20.

The absorbent core 26 may be any absorbent material which is generally compressible, conformable, non-irritating to the wearer's skin, and capable of absorbing and retaining liquids and certain body exudates. The absorbent core 26 may be manufactured in a wide variety of sizes and shapes (e.g., rectangular, hourglass, asymmetric, etc.) and from a wide variety of liquid absorbent materials commonly used in disposable diapers and other absorbent articles, such as comminuted wood pulp which is generally referred to as airfelt. Examples of other suitable absorbent materials include creped cellulose wadding, absorbent foams, absorbent sponges, superabsorbent polymers, absorbent gelling materials, or any equivalent materials or combination of materials. The total absorbent capacity of the absorbent core 26 should, however, be compatible with the intended use of the diaper 20. Further, the absorbent capacity and configuration of the absorbent core 26 may be varied to accommodate wearers ranging from infants through adults (e.g., the absorbent core may have a varying caliper, or hydrophilic gradient, a capillary differential, low density zones, or may or may not contain absorbent gelling materials).

The absorbent core 26 may comprise a layer of absorbent material comprising hydrophilic fibers and particles of absorbent gelling material (hydrogel) such as the absorbent structure described in U.S. Pat. No. 4,610,678 entitled "High-Density Absorbent Structure" which issued to Paul T. Weisman and Steven A. Goldman on Sep. 9, 1986 and which patent is incorporated herein by reference. Preferred embodiments of the absorbent core 44 are generally described in U.S. Pat. No. 5,234,423 entitled "Absorbent Article With Elastic Waist Feature and Enhanced Absorbency", issued to Alemany et al. on Aug. 10, 1993; and U.S. Pat. No. 5,217,445 entitled "Absorbent Structures Containing Superabsorbent Material and Web of Wetlaid Stiffened Fibers" issued to Young et al. on Jun. 8, 1993, which are incorporated herein by reference. Other exemplary absorbent cores useful in the present invention are described in U.S. Pat. No. 5,124,188 entitled "Porous, Absorbent, Polymeric Macrostructures and Methods of Making the Same", issued to Roe et al., on Jun. 23, 1992; U.S. Pat. No. 5,137,537 entitled "Absorbent Structure Containing Individualized., Polycarboxylic Acid Crosslinked Wood Pulp Cellulose Fibers", issued to Herron et at., on Aug. 11, 1992; U.S. Pat. No. 5,180,622 entitled "Absorbent Members Containing Interparticle Crosslinked Aggregates", issued to Berg, et at., on Jan. 9, 1993; U.S. Pat. No. 5,260,345 entitled "Absorbent Foam Materials for Aqueous Body Fluids and Absorbent Articles Containing Such Materials" issued to DesMarais et al., on Nov. 9, 1993; U.S. Pat. No. 4,673,402 entitled "Absorbent Article With Dual-Layered Cores" which issued to Paul T. Weisman, Dawn I. Houghton and Dale A. Gellert on Jun. 16; and PCT Publication No. WO 92/11830, published on Jul. 23, 1992, entitled "Absorbent Article Having Rapid Acquiring, Multiple Layer Absorbent Core". All of these patents and publications are hereby incorporated herein by reference.

The topsheet 22 is preferably. compliant, soft feeling, and non-irritating to the wearer's skin. Further, the topsheet 22 is preferably liquid pervious permitting liquids to readily penetrate through its thickness. A suitable topsheet may be manufactured from a wide range of materials, such as porous foams, reticulated foams, formed films, apertured plastic films, natural fibers (e.g., wood or cotton fibers), synthetic fibers (e.g., polyester or polypropylene fibers) or from a combination of natural and synthetic fibers. There are a number of manufacturing techniques which may be used to manufacture the topsheet 22. For example, the topsheet 22 may be woven, nonwoven, spunbonded, carded, or the like. One preferred topsheet 22 comprises polypropylene fibers having a denier of about 2.2, such as P-8, manufactured by Veratec, Inc., a Division of the International Paper Company, of Walpole, Mass. A preferred topsheet 22 is carded, and thermally bonded by means well known to those skilled in the fabrics art.

Preferably, the topsheet 22 is made of a hydrophobic material to isolate the wearer's skin from liquids in the absorbent core 26. If the topsheet 22 is made of a hydrophobic material, at least the upper surface of the topsheet 22 is treated to be hydrophilic so that liquids will transfer through the topsheet 22 more rapidly. This diminishes the likelihood that body exudates will flow off the topsheet 22 rather than being drawn through the topsheet 22 and being absorbed by the absorbent core 26. The topsheet 22 can be rendered hydrophilic by treating it with a surfactant including spraying the topsheet 22 material with a surfactant or immersing the material into the surfactant. A more detailed discussion of such a treatment is contained in U.S. Pat. No. 4,988,344 entitled "Absorbent Articles with Multiple Layer Absorbent Layers" issued to Reising et al., on Jan. 29, 1991, and U.S. Pat. No. 4,988,345 entitled "Absorbent Articles with Rapid Acquiring Absorbent Cores" issued to Reising on Jan. 29, 1991, each of which is incorporated herein by reference.

The topsheet 22 and the backsheet 24 may be joined together in any suitable manner as is well known in the diaper manufacturing art. As used herein, the term "joined" encompasses configurations whereby the topsheet 22 is directly joined to the backsheet 24 by affixing the topsheet 22 directly to the backsheet 24, and configurations whereby the topsheet 22 is indirectly joined to the backsheet 24 by affixing the topsheet 22 to intermediate members which in turn are affixed to the backsheet 24. In a preferred embodiment, the topsheet 22 and the backsheet 24 are joined directly to each other in the diaper periphery 35 by an adhesive or any other attachment means as is known in the art. Alternative suitable attachment means are discussed below with regard to the backsheet 24.

The backsheet 24 is preferably positioned adjacent the garment surface 60 of the absorbent core 26 that faces away from the wearer and is preferably secured s thereto by attachment means such as those well known in the art. (However, embodiments are contemplated wherein at least a portion of the backsheet 24 is not joined to the absorbent core 26, preferably adjacent the landing zone 40.) For example, the backsheet 24 may be secured to the absorbent core 26 by a uniform continuous layer of adhesive, a patterned layer of adhesive, or an array of separate lines or spots of adhesive. Alternatively, the attachment means may comprise heat bonds, pressure bonds, ultrasonic bonds, dynamic mechanical bonds, or any other suitable attachment means or combinations of these attachment means as are known in the art. An adhesive which has been found to be satisfactory is manufactured by H. B. Fuller Company of St. Paul Minn. and marketed as HL-1258. The core is attachment means preferably comprise an open pattern network of filaments of adhesive as is shown in U.S. Pat. No. 4,573,986 entitled "Disposable Waste-Containment Garment" which issued to J. A. Minetola and David R. Tucker on Mar. 4, 1986, and which is incorporated herein by reference. An exemplary attachment means of an open pattern network of filaments comprises several lines of adhesive filaments swirled into a pattern such as is illustrated by the apparatus and methods shown in U.S. Pat. No. 3,911,173 issued to Sprague, Jr. on Oct. 7, 1975; U.S. Pat. No. 4,785,996 issued to Zieckler, et al. on Nov. 22, 1978; and U.S. Pat. No. 4,842,666 issued to Werenicz on Jun. 27, 1989. Each of these patents are incorporated herein by reference.

Figure 2:
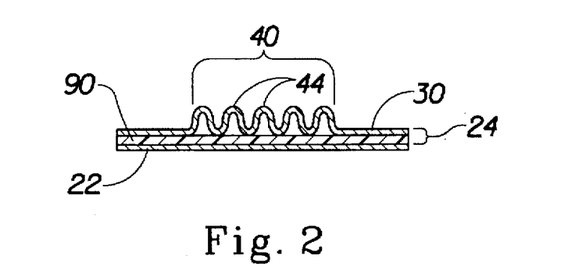
FIG. 2 is a cross-sectional view of the disposable diaper shown in FIG. 1.

In a preferred embodiment, the backsheet 24 includes a laminate of at least two webs, an inner web 90 and an outer web 30, as shown in FIG. 2. At least a portion of the inner web 90 is preferably located adjacent the garment surface 60 of the absorbent core 26. The inner web 90 preferably acts as a barrier to prevent liquids from passing through the backsheet 24 while the outer web 30 preferably provides for an integral landing zone 40 as well as aesthetic and emotional qualities such as softness and cloth-like appearance. Accordingly, in preferred embodiments, the inner web 90 of the backsheet 24 preferably includes a thin plastic film or other flexible liquid impervious or hydrophilic materials. (As used herein, the term "flexible" refers to materials which are compliant and which will readily conform to the general shape and contours of the human body.) It may also be desirable for the backsheet 24 to be breathable, thus, permitting vapors to escape from the absorbent core 26 while still preventing exudates from passing through the backsheet 24. An exemplary film for use in inner web 90 of the backsheet 24 is a polyethylene film having a thickness of from about 0.012 mm (0.5 mil) to about 0.051 cm (2.0 mils). Suitable polyethylene films are manufactured by Tredegar Film Products, Inc. of Terre Haute, Ind. and the Clopay Corporation of Cincinnati, Ohio marketed under the trade names Tredegar X8526 and Clopay 1401, respectively. Exemplary nonwovens for use as the outer web 30 are the nonwoven web materials P-8 or P-11 manufactured by Veratec, Inc. a division of the International Paper Company of Walpole, Mass. Alternative materials for use in the inner web 90 include woven webs, formed films, apertured films, foams, scrims and the like.

The outer web 30, as mentioned above, is that portion of the backsheet 24 which is on the outside surface of the absorbent article. Thus, the outer web 30 should have certain characteristics. For example, the outer web 30 should provide good aesthetic and emotional qualities such as softness and a cloth-like appearance. Further, the outer web 30 should include materials which can be made to engage the hooks or other engaging elements 72 of a male fastening component 70. Generally, such materials include fibers, fibrous nonwoven materials, apertured materials, formed films, woven materials, foams, scrims and the like. Two suitable nonwovens for use as the outer web 30 are the nonwoven web materials P-8 or P-11 manufactured by Veratec, Inc. a division of the International Paper Company of Walpole, Mass.

The outer web 30 is preferably laminated to the inner web 90 by means known in the art. The term "laminated", as used herein, refers to webs which have their coincident surfaces bonded to each other so as to provide a integral web of material. The area of the bonding may range from as little as 5% of the surface area of the coincident surfaces to as much as 100% of the coincident surfaces. (When one or more rough or uneven surfaces are bonded, such as when nonwovens, apertured films and the like are joined, laminating occurs when the materials are bonded where the materials contact each other when they are in a flat-out face to face configuration.) Examples of suitable lamination means may include all-over gluing, spiral gluing, meltblown gluing, screen or gravure printing, heat, pressure, vacuum forming, extrusion coating or ultrasonic bonding.

Backsheet 24 preferably also includes an integral landing zone 40. As used herein, the term "integral" when referring to the landing zone 40 means that the landing zone 40 is formed from at least a portion of the structure of the backsheet 24. Thus, the integral landing zone 40 of the present invention needs no additional material to provide the entangling characteristics of an effective female fastening component. Rather, the integral landing zone 40 includes a portion or portions of the backsheet 24 which is mechanically prestrained or otherwise altered to provide the raised elements 44 which are capable of entangling the engaging elements 72 of a complementary male fastening component 70. Such mechanical alteration of the backsheet 24 can be easily provided on or off the diaper manufacturing line at high speeds and low cost. (The term "mechanically prestrained" refers to a method by which portions of a web are subjected to some degree of localized mechanical stretching which permanently elongates the mechanically prestrained region of the web.)

FIG. 2 is a cross-sectional view taken along line 2—2 of FIG. 1 which depicts a preferred construction of the backsheet 26 including integral landing zone 40. As shown, it is preferred that the mechanically prestrained portion of the outer web 30 is located at least partially in the front waist region 52 of the diaper 20 such that male fastening components 70 joined to the rear of the diaper 20 may engage the landing zone 40 and provide side closures for the diaper 20. However, other embodiments are contemplated wherein the landing zone 40 is located outside of the front waist region 52, or more than one landing zone 40 is used to provide a broader fit range or disposal means.

In preferred embodiments of the present invention, the mechanically prestrained portion(s) of the outer web 30 are not laminated to the inner web 90 as described above. Most preferably, the inner web 90 and the outer web 30 are not bonded to each other in the landing zone 40. However, embodiments are contemplated wherein the inner web 90 and the outer web 30 are intermittently bonded to each other in the landing zone 40. As used herein, the term "intermittently bonded" refers to webs which are bonded together with one or more individual, discrete bonds that are not continuous or bond patterns having open areas free of bonds. In preferred embodiments, the intermittent bonding of the mechanically prestrained portions of the outer web 30 and the inner web 90 joins less than about 90% of the plan view area of the webs' coincident surfaces. More preferably, the intermittent bonding joins less than about 70% of the plan view area of the coincident surfaces and most preferably, the intermittent bonding joins less than about 25% of the plan view area of the coincident surfaces. Examples of suitable intermittent bonding patterns are shown and described in co-pending U.S. patent application Ser. No. 08/287,571, filed Aug. 9, 1994 in the names of King, et al., now U.S. Pat. No. 5,595,567. The disclosure and drawings of the King et al. application is hereby incorporated by reference herein. The use of intermittent bonds or no bonds between the landing zone 40 of the outer web 30 and the inner web 90 permits the raised portions 44 of the landing zone 40 to retain all or some of the loft created by the prestraining method. This helps ensure that the landing zone 40 is capable of receiving and entangling the engaging elements 72 of the male fastening component 70.

To further increase the peel strength of the fastening system 50 of the present invention, it may be desirable to have the portion of backsheet 24 adjacent the landing zone 40 unattached to the immediately adjacent layer, e.g., absorbent core 26. By having the portion of the backsheet 24 adjacent the landing zone 40 unattached to the immediately adjacent layer, the backsheet 24 will raise or lift independently from the landing zone 40 which will also raise and lift upon separation of the hooks from the loops of the landing zone 40, thereby further increasing the peel strength of the fastening system 50.

Figure 7:
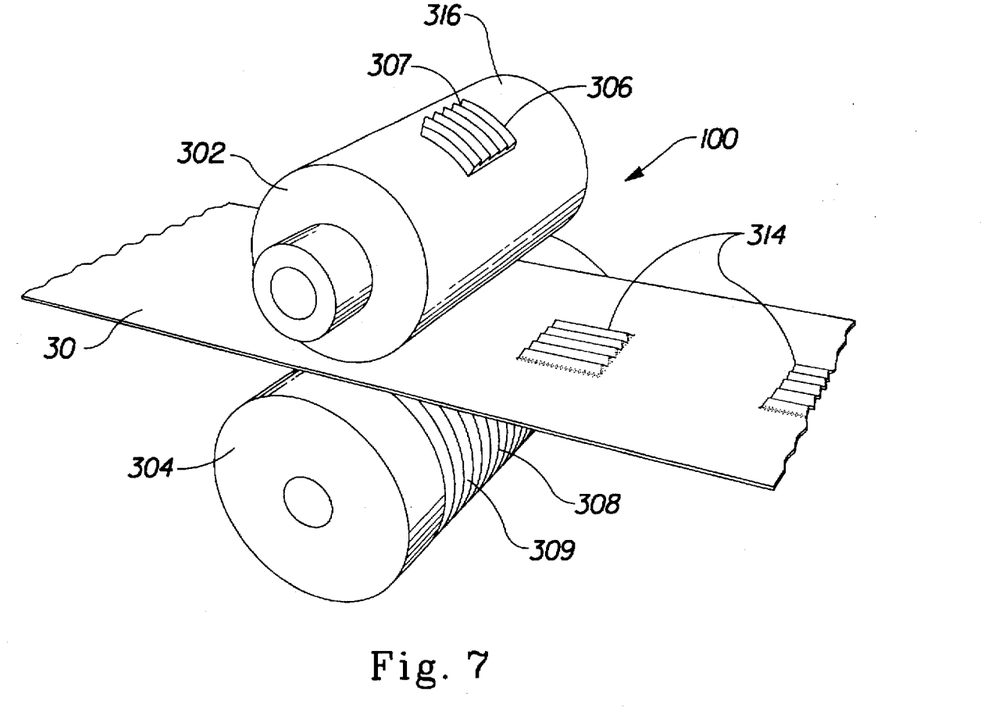
FIG. 7 is a perspective view of a portion of the apparatus for making the present invention.

Although any known means for elongating webs can be used to provide the raised portions 44 of the landing zone 40, incremental mechanical stretching methods generally provide adequate results. For example, the inner web 30 may be directed through one or more rollers having groves or teeth which act to incrementally elongate the desired regions of the web. Alternatively, the inner web 30 may be subjected to other ring-rolling or deep embossing techniques as are known in the art. Some exemplary incremental stretching methods are described in U.S. Pat. No. 5,151,092 issued to Buell et al on Sep. 29, 1992; U.S. Pat. No. 5,143,679 entitled "Method For Sequentially Stretching Zero Strain Stretch Laminate Web To Impart Elasticity Thereto Without Rupturing The Web" issued to Webber et al on Sep. 1, 1992 and U.S. Pat. No. 5,518,801 entitled "Web Materials Exhibiting Elastic-Like Behavior", which issued to Chappell et al. on May 21, 1996. Each of these patents is hereby incorporated herein by reference. One preferred incremental stretching system 100 is shown in FIG. 7 which is described in more detail below.

Figure 3:
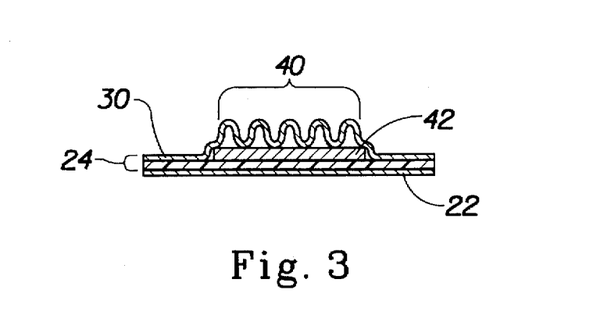
FIG. 3 is a cross-sectional view of an alternative embodiment of the present invention.
Figure 4:
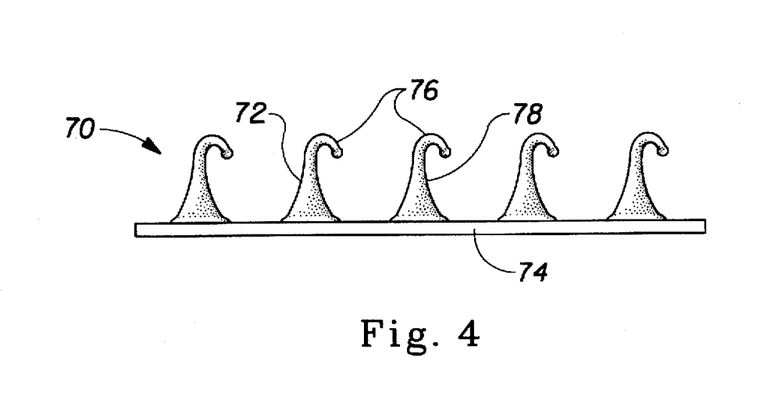
FIG. 4 is a greatly enlarged side view of a male fastening component.

FIG. 3 is a cross-sectional view of an alternative embodiment of the present invention including loft element 42. The loft element 42, located between the inner web 90 and at least some of the raised portions 44 of the integral landing zone 40, spaces the raised portions 44 away from the inner web 90. This spacing provides the landing zone 40 with greater thickness which can increase the effectiveness of the fastening system 50. For example, the loft element 42 may provide space for the engaging elements 72 of the male fastening component 70 to penetrate into the raised elements 44 such that the landing zone 40 can more effectively entangle the engaging elements 72. Thus, the loft element 42 is especially advantageous when the outer web 30 includes a relatively low basis weight nonwoven web which has little loft even after it has been mechanically strained and/or when the inner web 90 includes a relatively dense material or a material with few openings to allow the engaging elements 72 to properly penetrate the raised portions 44 of the integral landing zone 40.

The loft element 42 may include any material known in the art which is capable of receiving the engaging components 72 of the male fastening component 70. In preferred embodiments, the loft element 42 has numerous open spaces in its structure so as to provide space for the engaging elements 72. Suitable materials for use as the loft element include nonwoven and woven webs, foams, apertured films, formed films, scrims, fibers, paper products or any other material or combination of materials capable of creating loft. (As used herein, the term "loft" refers to spacing in the z-direction. For example, the ,loft provided by a nonwoven web laminated between two other webs would be the thickness of the nonwoven web.) Some examples of loft elements are described in U.S. Pat. No. 5,407,439 entitled "Multilayer Female Component For Refastenable Fastening Device and Method of Making the Same" issued to David J. K. Goulait on Apr. 18, 1995, which is hereby incorporated by reference herein.

Embodiments including a loft element 42 may be configured in any number of ways so long as the raised portions 44 of the integral landing zone 40 are capable of entangling the engaging elements 72 of the male fastening component 70. For example, the mechanically prestrained portion of the outer web 30 including the raised portions 44 may be continuously or intermittently joined with the loft element 42, or may not be joined to the loft element 42 at all. Further, the loft element 42 may be continuously or intermittently joined to the inner web 90, or may be held in place by the lamination of the inner web 90 and the outer web 30 around the loft element 42. Also, the loft element 42 may be located such that it is adjacent all or any portion of the outer web 30 which has been prestrained.

Figure 8:
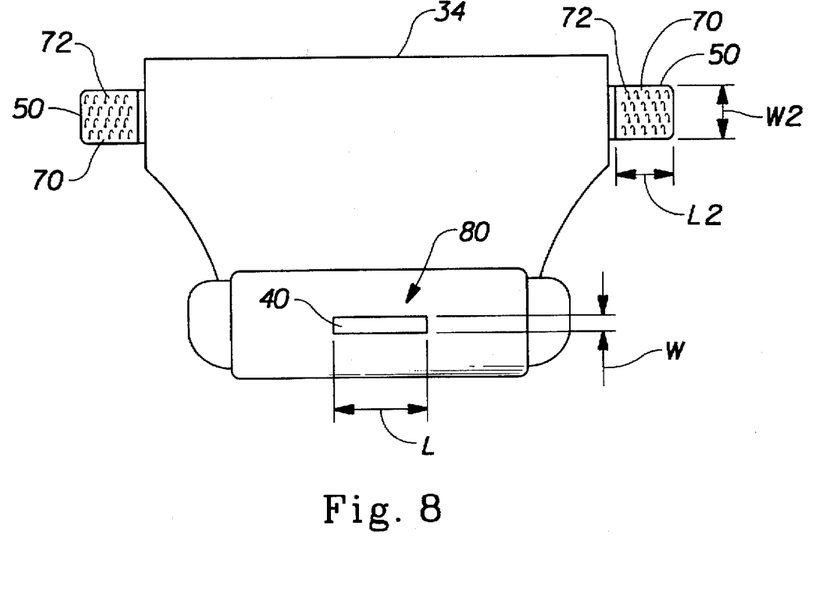
FIG. 8 is a perspective view of one embodiment of the present invention.

In some embodiments, the landing zone 40 will have a first fastening area A which is larger than the second fastening area B comprised by the engaging elements 72 of the male component 70. The larger landing zone 40 generally facilitates convenient fastening for broad ranges of wearers. (As shown in FIG. 8, the landing zone first fastening area A is equal to the length L of the landing zone 40 times the width W of the landing zone 40. The male component second fastening area B is equal to the length L2 times the width W2. The areas of complex shapes can be determined by known mathematical formulas. If multiple landing zones or male components are comprised in a single functional primary or disposal fastening system, the area (A or B) equals the sum of the individual elements. However, the area of a disposal landing zone 80 generally will not include the area of the primary landing zone and vice versa.) Alternatively, the landing zone first fastening area A may be smaller than the male component second fastening area B. As an example, a disposal fastening system of a disposable absorbent article often require less fastening strength than the primary fastening system. The low cost landing zone 40 of the present invention provides a means by which a relatively small landing zone 40 can be integrated into the backsheet 24 for disposal fastening.

The Complementary Male Component

The term "male component", as used herein, is used to designate the portion of the fastening system 50 having engaging elements 72, such as books. The male fastening components 70 may include conventional, commercially available hook materials, but are not limited to such conventional hooks. For example, the engaging elements 72 may have any shape known in the art such as hooks, "T's", mushrooms, prongs or any other shape. Further, the male component 70 may be manufactured from a wide range of materials. Such suitable materials include, but are not limited to, nylon, polyester, polypropylene, or any combination of these or other materials. One suitable male component 70 may comprise a number of shaped engaging elements projecting from a woven backing 74 such as the commercially available material designated "SCOTCHMATE" brand No. FJ3402 available from Minnesota Mining and Manufacturing Company, St. Paul, Minn. A preferred male component is described in U.S. Pat. 4,846,815 entitled "Disposable Diaper Having An Improved Fastening Device" which issued to C. L. Scripps on Jul. 11, 1989. Other particularly preferred male components and methods for making the same are the prongs described in U.S. Pat. 5,058,247 entitled "Mechanical Fastening Prong" issued to Thomas et al. on Oct. 22, 1991; U.S. Pat. No. 5,116,563 entitled "Process for Producing a Mechanical Fastener" issued to Thomas et al. on May 26, 1992; U.S. Pat. No. 5,180,534 entitled "Process of Manufacturing A Refastenable Mechanical Fastening System", which issued to Thomas, et al. on Jan. 19, 1993; and U.S. Pat. 5,230,851 entitled "Process of Manufacturing a Refastenable Fastening System" issued to Thomas on Jul. 27, 1993. Each of these patents are hereby incorporated by reference herein.

Figure 6:
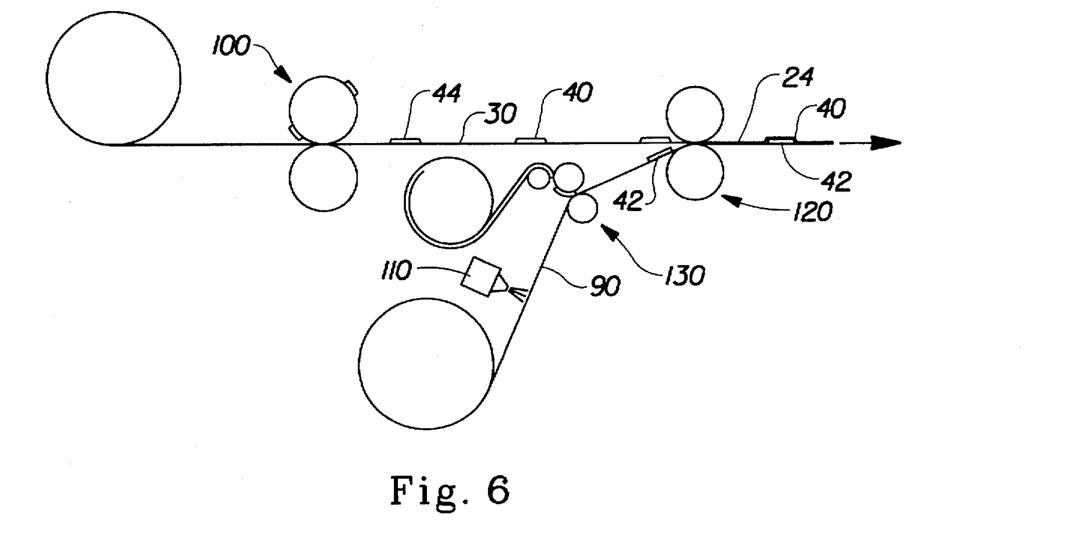
FIG. 6 is a perspective view of a process for making an alternative embodiment of the backsheet of the present invention including an integral landing zone.

An example of a suitable male fastening component 70 is shown in FIG. 6. Preferably, the male fastening component 70 includes a plurality of engaging elements 72 extending outwardly from a backing 74. Each engaging element 72 preferably includes a stem 78 and a head 76. The stem 78 is that portion of the engaging element 72 which is adjacent the backing 74 and which supports the head 76. The head 76 is that portion of the engaging element 72 which is spaced apart from the backing 74 such that it may penetrate and engage the "loops" of a female fastening component. In the present invention, the engaging elements 72 of the male fastening component 70 preferably penetrate and entangle the raised portions 44 of the integral landing zone 40.

Method of Making the Backsheet including the Integral Landing Zone

The method for making the backsheet 24 of the present invention including an integral landing zone 40 is very simple and cost effective. The following method may be integrated into a diaper line or may occur at a time and location different from the manufacture of the article to which the backsheet 24 is being joined. Although only a few suitable embodiments of the method for making the backsheet of the present invention are described in detail herein, it should be noted that substitution of any or all of the process steps for steps which provide similar results are contemplated as are processes which include similar steps in different orders.

Figure 5:
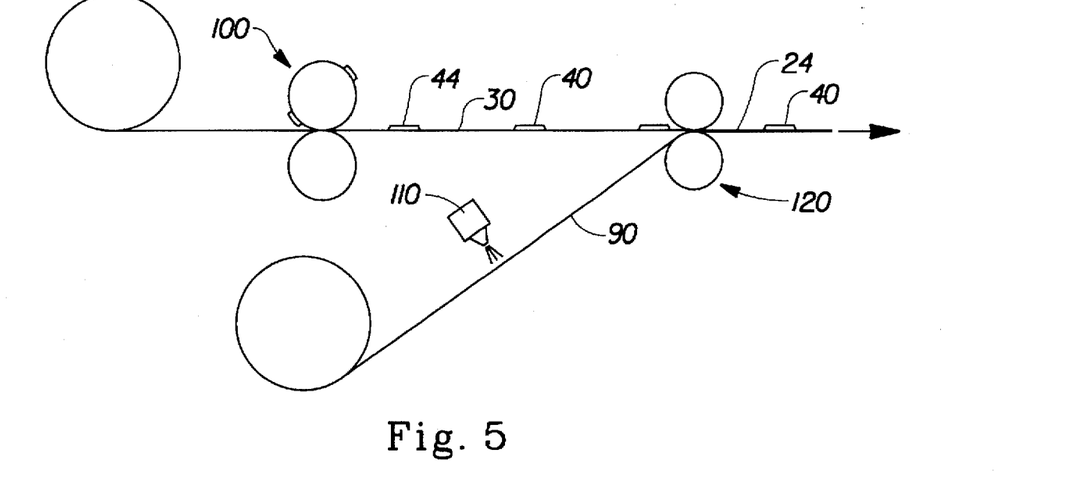
FIG. 5 is a schematic side view of a process for making the backsheet of the present invention including the integral landing zone.

FIG. 5 illustrates one example of the method for making the backsheet 24 of the present invention having an integral landing zone 40. Outer web 30 and inner web 90 are provided from storage rolls or from other parts of the manufacturing process. Outer web 30 is directed through a mechanical prestraining device 100. The mechanical prestraining device 100 stretches and permanently elongates at least a portion of the outer web 30 to form raised elements 44. Stretching device 100 preferably includes a pair of intermeshing incremental stretching rolls 302 and 304. Roller 302 preferably includes a plurality of teeth 306 and corresponding grooves 307 which intermesh with or engage grooves 309 on roller 304. As a web, such as outer web 30, is passed between incremental stretching rollers 302 and 304, the web 30 is stretched and/or elongated producing incrementally stretched regions 314. The incrementally stretched regions 314 of the outer web 30 form raised elements 44. The portion of the web 30 passing between the smooth portions 316 of the roller 302 and the roller 304 will be generally unstrained and thus, will become that portion of the outer web 30 which is joined directly to the inner web 90 to form the backsheet 24. The exact configuration, spacing, dimensions, and overlap of opposing teeth and grooves can be adjusted to change the height, location and density of the raised elements 44. Further, the incremental stretching may be in the machine direction, the cross-machine direction or in directions other than the machine direction or the cross-machine direction.

Inner web 90 is passed through an adhesive coater 110 which applies adhesive to one surface of the inner web 90. (It should be noted that the adhesive coater 110 may be replaced by another device for applying joining means to either the inner web 90 or the outer web 30. Such may be the case if alternative bonding means were being used such as ultrasound, heat, pressure or the like.) The inner web 90 and the outer web 30 are then passed through rollers 120 which direct the webs into face to face contact with each other. The webs exit the rollers in a laminated condition with the outer web 30 having raised elements 44 which provide the backsheet laminate 24 an integral landing zone 40. Preferably, the lamination process leaves at least a portion of the outer web 30 including the raised elements 44 free of adhesive or other bonding means such that the landing zone 40 is created with enough loft to receive and entangle the engaging elements 72 of a male fastening component 70.

In an alternative embodiment, as shown in FIG. 6, the additional loft member 42 is provided by the cut and slip unit 130 or any other device as is known in the art. As above, outer web 30 is directed through a prestraining device to elongate at least that portion of the web which will constitute the landing zone 40. Inner web 90 has an adhesive or other joining means applied and loft element 42 is joined thereto. The inner web 90 is then laminated to the outer web 30 with the loft element positioned to space at least a portion of the landing zone 40 away from the inner web 90. It should be noted that alternative bonding means are contemplated as well as configurations where the loft element is joined to the outer web 30 or neither the inner web 90 or the outer web 30.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable absorbent article having a front waist region, a rear waist region and a crotch region located between said front waist region and said rear waist region, the absorbent article comprising:

a liquid pervious topsheet;

a liquid impervious backsheet joined with said topsheet; and an absorbent core located between said topsheet and said backsheet, said absorbent core having a garment surface and a body surface;

said backsheet including an inner web and an outer web, at least a portion of said inner web being juxtaposed said garment surface of said absorbent core, said outer web including, an integral landing zone having portions mechanically prestrained to provide raised elements capable of entangling the engaging components of a complementary male fastening component;

said inner web and said outer web being bonded together except in said landing zone.

2. The disposable absorbent article of claim 1 wherein said outer web is a nonwoven web.

3. The disposable absorbent article of claim 1 wherein said mechanically prestrained portion of said outer web is intermittently bonded to said inner web.

4. The disposable absorbent article of claim 1 wherein said integral landing zone is located in at least a portion of said front waist region.

5. The disposable absorbent article of claim 4 further comprising complementary male fastening components disposed in said rear waist region such that when said male fastening components and said landing zone are releasably joined, side closures are formed.

6. The disposable absorbent article of claim 4 wherein at least a portion of said integral landing zone is disposed in said crotch region to provide disposal means.

7. The disposable absorbent article of claim 1 wherein at least a portion of said integral landing zone is disposed in said rear waist region to provide disposal means.

8. The disposable absorbent article of claim 1 further including a loft element disposed between said mechanically prestrained portion of said outer web and said inner web.

9. The disposable absorbent article of claim 8 wherein said outer web is intermittently joined to said loft element.

10. The disposable absorbent article of claim 8 wherein said loft element is selected from the following group: nonwoven web, foam, formed film, scrim or apertured film.

11. The disposable absorbent article of claim 1 wherein said landing zone has a first fastening area and said male fastening component has a second fastening area, said first fastening area being less than said second fastening area.

12. A disposable absorbent article having a front waist region, a rear waist region and a crotch region located between said front waist region and said rear waist region, the absorbent article comprising:

a liquid pervious topsheet;

a liquid impervious backsheet joined with said topsheet; and an absorbent core located between said topsheet and said backsheet, said absorbent core having a garment surface and a body surface;

said backsheet including:

an inner web disposed adjacent at least a portion of said garment surface of said absorbent core;

an outer web laminated with said inner web, said outer web including an integral landing zone having mechanically prestrained portions to provide raised elements capable of entangling the engaging components of a complementary male fastening component; and a loft element disposed between said inner web and at least a portion of said mechanically prestrained portion of said outer web, said loft element spacing said landing zone portion of said outer web away from said inner web.

13. The disposable absorbent article of claim 12 wherein said outer web is a nonwoven web.

14. The disposable absorbent article of claim 13 wherein said integral landing zone is located in at least a portion of said front waist region.

15. The disposable absorbent article of claim 12 further comprising complementary male fastening components disposed in said rear waist region such that when said male fastening components and said landing zone are releasably joined, side closures are formed.

16. The disposable absorbent article of claim 12 wherein at least a portion of said integral landing zone is disposed in said crotch region to provide disposal means.

17. The disposable absorbent article of claim 12 wherein at least a portion of said integral landing zone is disposed in said rear waist region to provide disposal means.

18. The disposable absorbent article of claim 12 wherein said outer web is intermittently joined to said loft element.

19. The disposable absorbent article of claim 12 wherein said loft element is selected from the following group: nonwoven web, foam, formed film, scrim or apertured film.

20. The disposable absorbent article of claim 12 wherein said landing zone has a first fastening area and said male fastening component has a second fastening area, said first fastening area being less than said second fastening area.

21. A disposable absorbent article having a front waist region, a rear waist region and a crotch region located between said front waist region and said rear waist region, the absorbent article comprising:

a liquid pervious topsheet;

a liquid impervious backsheet joined with said topsheet, said backsheet including a laminate of an inner web and an outer web; and an absorbent core located between said topsheet and said backsheet, said absorbent core having a garment surface and a body surface, at least a portion of said garment surface of said absorbent core being located adjacent said inner web;

said backsheet including an integral landing zone consisting of a mechanically prestrained portion of said outer web having raised elements capable of entangling the engaging components of a complementary male fastening component.

22. The disposable absorbent article of claim 21 wherein said outer web is a nonwoven web.

23. The disposable absorbent article of claim 21 wherein said mechanically prestrained portion of said outer web is intermittently bonded to said inner web.

24. The disposable absorbent article of claim 21 wherein said integral landing zone is located in at least a portion of said front waist region.

25. The disposable absorbent article of claim 21 wherein at least a portion of said integral landing zone is disposed in said rear waist region to provide disposal means.

26. A disposable absorbent article having a front waist region, a rear waist region and a crotch region located between said front waist region and said rear waist region, the absorbent article comprising:

a liquid pervious topsheet;

a liquid impervious backsheet joined with said top sheet, said backsheet including a laminate of an inner web and an outer web;

an absorbent core located between said topsheet and said backsheet, said absorbent core having a garment surface and a body surface; and a male fastening component disposed in said rear waist region of said absorbent article, said male fastening component including a backing and a plurality of engaging elements extending therefrom; and an integral landing zone located in at least a portion of said front waist region, said integral landing zone comprising at least a portion of said outer web which is mechanically prestrained to provide raised elements capable of entangling the engaging components of said complementary male fastening component.

27. The disposable absorbent article of claim 26 wherein at least a portion of said integral landing zone is disposed in said crotch region to provide disposal means.

28. The disposable absorbent article of claim 26 wherein at least a portion of said integral landing zone is disposed in said rear waist region to provide disposal means.

29. The disposable absorbent article of claim 26 further including a loft element disposed between said mechanically prestrained portion of said outer web and said inner web.

30. The disposable absorbent article of claim 26 wherein said landing zone has a first fastening area and said male fastening component has a second fastening area, said first fastening area being less than said second fastening area.

* * * * *

UNITED STATES PATENT AND TRADEMARK OFFICE
CERTIFICATE OF CORRECTION

PATENT NO.   : 5,735,840
DATED        : April 7, 1998
INVENTOR(S)  : Mark J. Kline et al.

Page 1 of 1

It is certified that error appears in the above-identified patent and that said Letters Patent is hereby corrected as shown below:

Column 4,
Line 27, "et at." should read -- et al. --.
Line 30, "et at." should read -- et al. --.

Column 5,
Line 41, "the core is attachment" should read -- the core attachment --.

Column 9,
Line 19, "books" should read -- hooks --.

Signed and Sealed this

Twenty-fifth Day of December, 2001

Attest:

JAMES E. ROGAN
Attesting Officer
Director of the United States Patent and Trademark Office